United States Patent
Tung et al.

(10) Patent No.: US 6,787,678 B1
(45) Date of Patent: Sep. 7, 2004

(54) METHOD OF REMOVING WATER FROM HYDROFLUOROCARBON MANUFACTURING PROCESSES

(75) Inventors: Hsueh Sung Tung, Getzville, NY (US); Jason T. Stuck, San Jose, CA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/733,036

(22) Filed: Dec. 11, 2003

(51) Int. Cl.$^7$ .................. C07C 17/38; C07C 17/00; C07C 17/08; C07C 19/08
(52) U.S. Cl. .............. 570/177; 570/164; 570/165; 570/238; 570/262
(58) Field of Search ................ 570/164, 165, 570/177, 238, 262

(56) References Cited

U.S. PATENT DOCUMENTS

| | | | |
|---|---|---|---|
| 5,091,168 A | * 2/1992 | Nappa | 423/489 |
| 5,334,784 A | 8/1994 | Blake et al. | 570/165 |
| 5,723,702 A | 3/1998 | Kwon et al. | 570/177 |
| 6,101,818 A | 8/2000 | Thomas et al. | 62/85 |
| 6,103,944 A | 8/2000 | Blake et al. | 570/165 |
| 6,111,151 A | 8/2000 | Ewing et al. | 570/177 |

* cited by examiner

*Primary Examiner*—Elvis O. Price
(74) *Attorney, Agent, or Firm*—Colleen D. Szuch

(57) ABSTRACT

Disclosed are improved fluorination processes and fluorine-containing compositions which involve introducing to one or more fluorination process compositions a water reactive agent in an amount and under conditions effective to decrease the amount of water in that composition. The water reactive agent is preferably introduced to the fluorination process at a location downstream of the fluorination reaction, in amounts and under conditions effective to produce a relatively lower concentration of water in the composition, and preferably throughout the fluorination process.

21 Claims, No Drawings

US 6,787,678 B1

METHOD OF REMOVING WATER FROM HYDROFLUOROCARBON MANUFACTURING PROCESSES

FIELD OF THE INVENTION

This invention relates to processes for the production of fluorinated organic compounds. More particularly, the present invention relates methods for producing fluorine-containing compositions containing advantageously low levels of water.

BACKGROUND OF THE INVENTION

There are numerous processes directed to the manufacture of fluorinated organic compounds and to compositions containing such compounds. Many of these processes involve the reaction of an organic compound, such as a chloroalkane or chloroalkene, with hydrogen fluoride (HF) in the presence of a fluorination catalyst. In several of these processes, water is present in one or more of the reaction product streams containing the desired fluorinated organic compound. This water may originate as an impurity in the reactants or other starting materials. The water also may be formed as a byproduct from the reaction process, including reaction of HF with the catalyst, and/or as a product of the catalyst regeneration process.

It has been recognized that mixtures of water and hydrogen fluoride are especially corrosive, and that this combination is both difficult and expensive to handle. As a result, it is typically desirable to remove water from those portions of the fluorination processes where it is exposed to HF, including in product streams, byproduct streams, reactant streams, and recycle streams. Moreover, water which is present in the fluorination process, even at low levels, may act as a catalyst poison, thereby having deleterious effects on the effectiveness, efficiency, selectivity and/or yield of the fluorination reaction.

Several methods of removing or reducing the amount of water from fluorination process streams have previously been proposed. For example, U.S. Pat. No. 5,334,784 (Blake, et al.) and U.S. Pat. No. 6,103,944 (Blake, et al.), suggest distillation as a method for physically removing water from a fluorination process stream. U.S. Pat. No. 6,111,151 (Ewing, et al.) discloses phase separation as an alternative method of physically removing undesirable water from the process stream. In addition, drying agents such as sodium polyacrylate (U.S. Pat. No. 6,101,818, Thomas, et al.) and calcium chloride (U.S. Pat. No. 5,723,702, Kwon, et al.) have also been suggested as a means to absorb water from a process stream. While Blake, Ewing, and others in the field have attempted to remove water from the reaction product by using equipment and methods downstream of the fluorination reactor, such as those described above, these processes are inherently expensive. Moreover, known absorbents that are compatible with the fluorination reaction are not selective for water and therefore cannot generally be used to advantage during the fluorination process. Each of the aforementioned methods also pose a further disadvantage in that they can only remove water downstream of the process reaction, and therefore they are not effective for the removal of water at the reaction site and cannot prevent catalyst poisoning.

Process streams downstream of the fluorination reaction typically contain unreacted organic materials and unreacted HF in addition to the desired fluorinated compounds. To increase product yield, it is common to separate the un-reacted starting components from the product stream and to recycle HF and/or the under fluorinated components back to the reaction step. Because recycling tends to increase the concentration of water present during the fluorination reaction, it is advantageous to remove any water from the product stream prior to recycling.

SUMMARY OF THE INVENTION

The present inventors have come to appreciate a need in the art for an improved fluorination process and for improved fluorine-containing compositions, preferably fluorine substituted organic molecules having from about 2 to about 5 carbon atoms. We have discovered that this need can be satisfied by introducing to one or more fluorination process compositions a water reactive agent in an amount and under conditions effective to decrease the amount of water in that composition. By applying this teaching, the fluorination process and the products produced thereby can be improved. Furthermore, the present inventors have recognized that water can have a deleterious effect not only on the processing of the reaction product downstream of the reactor, but also on the fluorination reaction itself. In view of this recognition, applicants have discovered a fluorination process which preferably comprises introducing to the fluorination reaction process, preferably at a location proximate to the site of the fluorination reaction and/or upstream of the fluorination reaction, a water reactive agent in an amount and under conditions effective to produce a relatively lower concentration of water in the reaction mixture, and preferably throughout the fluorination process.

As used herein, the term "water reactive agent" refers to one or more elements and/or compounds which react either directly or indirectly through the production of intermediate compound(s), with water present at one or more locations in the fluorination process to effectively reduce the molecules of water present in the process stream or composition. As used herein, the term "fluorination process" is intended to refer to and include the fluorination reaction itself as well as upstream processing (such as preheating, catalyst treatment, and the like), and downstream processing (such as component separation and the like). Thus, the term "fluorination process" includes the location or site of the fluorination reaction and also the streams which are fed to or withdrawn from the reaction site or vessel. In preferred embodiments, the water reactive agent is reactive under conditions which exist at one or more locations in the fluorination process. In other words, the water reactive agent is preferably added to the fluorination process at one or more locations in the process without requiring any substantial alteration of the fluorination reaction conditions, and even more preferably also without requiring any substantial alteration of the upstream and downstream process conditions.

It is also generally preferred that present methods effectively reduce the amount of water at one or more locations in the fluorination process without introducing, directly or as a reaction product, any substantial amount of deleterious new compounds to the process. As used herein, a "deleterious compound" is one which is either not readily removed from the process or which must be introduced at a location in the fluorination process that has a negative effect on the operation of the fluorination reaction. For example, a water reactive agent which is a poison to the catalyst used in the process, or which causes the formation of a catalyst poison, would be considered a deleterious compound if such a water reactive agent must be inserted into the process at a location or under conditions which cause this negative effect on the fluorination reaction. A compound that is otherwise already present in the process would generally not be considered a deleterious compound. It is preferred in certain embodiments that the presence of the water reactive agent of the present invention does not cause the presence of any substantial amount a new reaction product to the fluorination process. As used herein, the term "new reaction product" refers to a compound or element that is otherwise not normally present in the fluorination reaction product stream or which would require a substantial alteration of the process to accommodate. Thus, it is optional in certain embodiments for the water reactive agent itself to comprise a compound, or combination of compound(s) and/or element(s) that are otherwise already present in the reaction product stream.

In preferred embodiments of the present invention, the water reactive agent comprises a compound having the formula I as follows:

$$XR_y \qquad (I)$$

where

X is C=O or S=O, each R is independently H, alkyl, or halogen, provided that at least one R is halogen, and y is 2.

In preferred embodiments, the water reactive agent comprises at least one compound containing a carbonyl or a thionyl group, more preferably a halogen substituted, aliphatic compound containing a carbonyl or a thionyl group, and even more preferably a chlorine substituted, aliphatic C1–C5 compound containing a carbonyl or a thionyl group. For the purpose of convenience, the terms $C_1$, C2, etc. are used herein to mean compounds having one carbon atom, two carbon atoms, etc.

DETAILED DESCRIPTION OF THE PREFERRED EMBODIMENTS

It is expected that effective water reactive agents can be formulated based on the presence of one or more compounds in accordance with the formula $XR_y$ as described above. In certain preferred embodiments, particularly those embodiments directed to the production of HFCs having from two to about five carbon atoms, such as for example pentafluoroethane (HFC-125) and tetrafluoroethane (HFC-134), the water reactive agent comprises a compound in which at least one R is chlorine. For compounds in which X is C=O, that is compounds having the general formula O=C—$R_2$, it is generally preferred that at least one R is chlorine. In highly preferred embodiments, the water reactive agent comprises phosgene ($COCl_2$). For embodiments in which X is S=O, it is also generally preferred that the R is chlorine, that is, that the water reactive agent comprises thionylchloride ($SOCl_2$).

The use of a water reactive agent in accordance with the present invention is highly preferred for use in processes in which the fluorination reaction is based on the fluorination of reactive organic compounds containing a chlorine substituted vinyl moiety and/or ethane, more preferably at least a dichlorine substituted vinyl moiety and/ethane, and even more preferably at least a trichlorine substituted vinyl moiety and/or ethane. For example, the present invention is especially well adapted to produce exceptional results when used in connection with the fluorination of perchloroethylene (PCE).

It is contemplated that, in view of the teachings contained herein, those skilled in the art will be able to identify without undue experimentation numerous water reactive agents that are adaptable for use in connection with the present methods, and all such reactive agents are within the broad scope hereof.

It is contemplated that the water reactive agent of the present invention can be introduced at essentially any location in the fluorination process and achieve removal of at least a portion of the water contained in the process. However, applicants appreciate that certain of the preferred water reactive agents, such as thionyl chloride, can have a deleterious effect on certain catalysts used in fluorination reactions. Accordingly, in many embodiments it is preferred that at least that portion of the water reactive agent which has a deleterious effect on the fluorination reaction, be introduced into a process stream located downstream of the reaction.

As is known to those skilled in the art, fluorination processes frequently produce recycle streams as a result of separation steps occurring downstream of the fluorination reaction. Accordingly, it is generally preferred that the processes of the present invention in which the water reactive agent comprises a potential catalyst poison, such as thionyl chloride, do not include a substantial recycle of the catalyst poison to the fluorination reactor. For example, in certain embodiments it is preferred to introduce the water reactive agent at a location in the process such that it will be consumed to a large extent, and preferably substantially fully consumed, in a chemical reaction, preferably with process water, at a point upstream of any substantial recycle stream. Alternatively or additionally, the process may be modified to include the step of avoiding recycle of water reactive agent by removing (by distillation or molecular sieve, for example) at least a substantial portion of the water reactive agent from the process at a point upstream of any substantial recycle stream.

Thus, it is preferred in many embodiments of the present invention that the methods preferably do not comprise the step of introducing the water reactive agent into the fluorination process at about the site of the fluorination reaction or otherwise to a location which will result in Exposure of the water reactive agent to the fluorination catalyst.

It will of course be appreciated by those skilled in the art that the various components of the water reactive agent need not be introduced together or at the same time or in the same manner to the fluorination process. The only requirement in this regard is that when multi-component water reactive agents are used, they are introduced into the process such that they can ultimately cooperate to react excess water out of the system, most preferably without introducing a substantial amount of any new reaction product to the system. It is believed that this process is effective for reducing the amount of water present in the process independent of the origin of the water. Because the preferred water removal agents and associated reaction products are chemical components already found in and/or readily removed from a fluorocarbon manufacturing process, no unusual contaminants are introduced. In preferred embodiments, the processes of the present invention produce a product stream which does not include a substantially amount of water, and which even more preferably is substantially water-free. It should also be appreciated that the step of introducing the water reactive agent to the process, unless indicted otherwise herein, should be construed broadly to include, for example, the step of introducing to the process a precursor to the water reactive agent which is converted during to the fluorination process to the water reactive agent.

The preferred embodiments of this invention thus provide methods for reducing the concentration of water in a reaction product stream produced by a fluorination reaction process by introducing into a stream downstream of the fluorination reaction mixture a water reactive agent, preferably phosgene, thionylchloride or a combination of these, in amounts sufficient and under conditions effective to substantially reduce the water in the composition of the product stream. Thus, while in certain embodiments it may be preferred to introduce the water reactive agent to the reaction mixture as a separate stream or as a component of one or more of the feed streams to the reactor, it is generally preferred that the water reactive agent is introduced into one or more of the effluent streams from the reactor. As used herein, the term "effluent stream" is intended to include not only those streams which exit directly from the reactor, but also those streams which are further downstream in the fluorination process.

According to a first aspect of the invention, methods are provided for reducing the amount of water in a fluorination process stream that comprises hydrogen fluoride (HF), reactive organic compounds, including for example perchloroethylene (PCE), and water in the form of moisture or otherwise. The process stream may also contain recycled byproducts of the fluorination reaction and possibly fluorinated organic compounds. In preferred embodiments, the water reactive agent, preferably comprising or consisting essentially of phosgene and/or thionylchloride, is introduced into a steam downstream of the reactor preferably without substantial alteration of the conditions otherwise existing in that process stream.

Although applicants do not wish to necessarily be bound by or limited to any particular theory of operation, it is believed that the preferred water reactive agents of the present invention, react under a wide range of conditions that exist in downstream fluorination processing, such as commonly exist in distillation units, strippers, and the like, with water to effectively remove a substantial portion of the water from such streams. In preferred embodiments, therefore, the water reactive agent is a compound or radical that includes and/or is converted under the conditions existing in the fluorination process, to an intermediate, compound or radical that reacts readily with water. A substantial portion of the water is thereby removed form the process stream.

The reaction mechanism by which the carbonyl compounds of the present invention remove the water (referred to as "process" water below) is believed to involve a reaction as illustrated below:

(a)

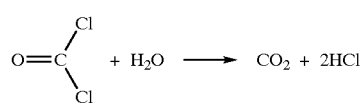

or (b)

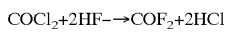

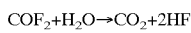

As can be seen from the above, the postulated possible reaction results in the water reactive carbonyl compound (phosgene or fluorinated phosgene in the illustrated reactions), to be reacted with process water under the applicable process conditions to carbon dioxide and HCl or HF, neither of which are deleterious to the process. It is contemplated that a similar reactions applies for reactive agent comprising thionyl compounds.

It is contemplated that a wide variety of reaction conditions are available to facilitate the water reaction in accordance with the present invention, and all such conditions are within the broad scope of the present invention. In preferred embodiments, however, the reaction by which the water is removed occur within a temperature range from about 20° C. (67° F.) to less than about 400° C. (752° F.) and a pressure of from about 0 psig to about 200 psig. More preferably, these reactions occur within a temperature range from about 25° C. (77° F.) to about 350° C. (662° F.), and even more preferably at about 50° C. (122° F.) to about 250° C. (482° F.).

The preferred concentration of the water reactive agent, and particularly phosgene, is in a molar ratio with the water present in the process where it is added, is from about 0.5:1 to about 5:1, and more preferably from about 1.5:1 to about 3:1, and even more preferably about 2:1.

Accordingly, the present invention provides a method for creating a process stream of fluorinated organic compounds essentially free of water. This process stream is created by adding a first co-feed of water reactive agent in accordance with the present invention to a fluorination process stream which contains more than trace amounts of water. The water reactive agent reacts in such a process stream according to the first aspect of the invention to reduce or substantially eliminate the water from the process stream. The fluorination process, as well as the water removal method, can be carried out in a wide variety of environments and in batch, continuous, and/or semi-continuous operations. It is generally preferred, however, that the methods are carried out in continuous or semi-continuous operations.

The principle operation of the preferred fluorination process is reacting a fluorination agent, such hydrogen fluoride (HF), with a reactive organic compound, more preferably halogenated hydrocarbons, even more preferably chlorinated hydrocarbons (CHC's), and most preferably chlorinated alkanes and alkenes. Examples of preferable chlorinated alkanes and alkenes include, but are not limited to, dichloromethane, vinyl chloride, dichloroethane, trichloroethane, dichloroethylene, trichloroethylene, tetrachloropropane, pentachloropropane, hexachloropropane, trichloropropylene, tetrachloropropylene, perchloroethylene, pentachlorobutane and the like. The product resulting from the preferred fluorination process of the present invention generally comprises chlorofluorocarbons (CFC's), hydrofluorocarbons (HFC's), hydrochlorofluorocarbons (HCFC's) and combinations of these. As desired, more than one hydrofluorocarbon may be produced in the process by co-production with another hydrofluorocarbon.

Many suitable catalytically active compounds are well known in the art, and include various inorganic compounds, for example oxides and halides of metals such as aluminum, cobalt, nickel, manganese, iron, chromium, antimony, tantalum, titanium, molybdenum and tin. A preferred embodiment of the present invention utilizes a chromium based catalyst in the fluorination process. In one embodiment of the invention in which a chromium based catalyst— is used, the fluorination reaction occurs in a range of temperature from about 100° C. (212° F.) to about 400° C. (752° F.), more preferably from about 300° C. (572° F.) to about 375° C. (707° F.), and even more preferably from about 320° C. (608° F.) to about 350° C. (662° F.). The operating pressure is preferably from about 0 psig to about 200 psig, with about 50 to 150 psig being most preferred in certain embodiments.

The water to be removed from the process stream may be introduced from one or more sources, such as water present in one or more of the reactants, water included or otherwise present in the catalyst, water produced as a result of interaction between one or more of the reactants and the catalyst (either fresh or regenerated), water produced during conditioning/regeneration of the catalysts, or water contained in any other medium introduced in the course of the reaction. Typically, the water content of the process stream will be from about 0.05 to about 5 wt. % based on the weight of the water and HF. Usually, prior to contact with the HF, the organic starting material will exist as a gaseous product stream at a temperature above the dew point of any water existing as an impurity in the HF starting component. In many embodiments it is preferred that the water reactive agent is exposed to a fluorination process stream that is at a temperature of from 100° C. (212° F.) and 250° C. (482° F.) in order to maximize the remove of the water.

The amount of water created as a byproduct of the fluorination process typically increases gradually as the reaction process progresses. The present invention preferably removes this water through the addition of a preferred water reactive agent into one or more compositions and/or process streams associated with the fluorination reaction, preferably at a location in downstream of the fluorination reactor. This can be achieved by adding the water reactive agent to one or more of the feeds to the vessel or unit operation or by introducing the agent separately to the vessel or unit operation. In preferred embodiments, the water reactive agent, such as phosgene and/or thionylchloride, hydrolyzes or reacts to form a reactant which hydrolyzes in the presence of water, thus removing the water from the process stream. The products of the reaction are then removed from the process by conventional means.

What is claimed is:

1. A method of removing water from a fluorination process comprising:
   a) providing at least one water reactive agent comprising a compound having the formula I:

   XR₂    (I)

where
   X is O=C or O=S, and
   each R is independently H, alkyl, or halogen, provided that at least one R is halogen
   b) providing in said fluorination process a composition containing a reactive organic compound, a fluorination agent and water; and
   c) introducing said water reactive agent into said composition under conditions effective to substantially reduce the concentration of water in said process.

2. A method of removing water from a fluorination process stream comprising:
   a) providing a process stream containing an organic compound, hydrogen fluoride, and water;
   b) introducing into said process stream a compound having the formula I:

   XR₂    (I)

where
   X is O=C or O=S, and
   each R is independently H, alkyl, or halogen, provided that at least one R is halogen; and
   c) reacting said compound with said water.

3. The method of claim 2 wherein X is O=C.

4. The method of claim 3 wherein each of said Rs are chlorine.

5. The method of claim 4 wherein the temperature of said process stream is from about 20° C. to less than about 350° C.

6. The method of claim 4 wherein the pressure of said process stream is from about 0 psig to about 200 psig.

7. The method of claim 5 wherein said compound is phosgene.

8. The method of claim 2 wherein X is O=S.

9. A method of making fluorinated organic compounds comprising the steps of:
   a.) reacting at least one organic reactive compound under conditions effective to fluorinate said organic reactive compound to produce a reaction effluent stream comprising water; and
   b.) introducing into said reaction effluent stream a water reactive agent comprising a compound having the formula I:

   XR₂    (I)

where
   X is OC or O=S, and
   each R is independently H, alkyl, or halogen, provided that at least one R is halogen said water reactive agent being effective under the conditions of said reaction effluent stream to remove at least a substantial portion of said water from said reaction effluent stream.

10. The method of claim 9 wherein said reacting step a) comprises a catalytic reaction.

11. The method of claim 10 wherein said reactive organic compound is a chlorinated vinyl compound.

12. The method of claim 11 wherein said chlorinated vinyl is ethylene having at least one chlorine substituent.

13. The method of claim 11 wherein said chlorinated vinyl compound comprises tetrachloroethylene.

14. The method of claim 10 wherein said compound is present in an amount sufficient to produce a compound:water molar ratio of from about 0.5:1 to about 3:1.

15. The method of claim 10 wherein a substantial portion of any water present in the reaction effluent stream is removed.

16. The method of claim 10 wherein said reaction step a) comprises reacting said reactive organic compound with hydrogen fluoride in the presence of a fluorination catalyst to form a fluorinated organic compound product stream containing a water by-product.

17. The method of claim 16 wherein said reactive organic compound is a chlorinated vinyl compound.

18. The method of claim 16 wherein said fluorination catalyst comprises chromium.

19. The method of claim 10 wherein the fluorinated organic compound is a hydrofluorocarbon.

20. The method of claim 10 wherein the fluorinated organic compound is a hydrochlorofluorocarbon.

21. A method of removing water from a fluorination process of the type having a process stream containing a reactive organic compound, a fluorination agent and water, the method comprising introducing at least one water reactive agent selected from the group consisting of a compound containing a carbonyl group, a thionyl group and combinations of these into said process stream under conditions effective to substantially reduce the concentration of water in said process.

* * * * *